United States Patent [19]

Huffman et al.

[11] 4,314,944

[45] Feb. 9, 1982

[54] 4-AMINOALKYL-7-HYDROXY-2(3H)-INDOLONES

[75] Inventors: William F. Huffman, Malvern; James W. Wilson, Wayne, both of Pa.

[73] Assignee: SmithKline Corporation, Philadelphia, Pa.

[21] Appl. No.: 180,551

[22] Filed: Aug. 22, 1980

[51] Int. Cl.³ .................... C07D 209/14; A61K 31/40
[52] U.S. Cl. .......................... 260/326.15; 260/326.16; 424/274
[58] Field of Search ...................... 260/326.16, 316.15; 424/274

[56] References Cited

U.S. PATENT DOCUMENTS 3,280,145  10/1966  Hofmann et al. .............. 260/326.15
3,644,403  2/1972   Canas-Rodriquez ........... 260/326.15
4,053,613  10/1977  Rounyak et al. ............... 260/326.16

FOREIGN PATENT DOCUMENTS 823841    4/1975  Belgium .
52-118465 10/1977 Japan .

OTHER PUBLICATIONS

Walker et al., J. Med. Chem. 13, pp. 983–985 (1970).
Loudon et al., Chem. Abst., 50, p. 4963 (1956).
Wahl, Chem. Abst., 12, p. 2196 (1918).
Yoshizaki et al., J. Med. Chem., 19, pp. 1138–1141 (1976).
Yoshizakai et al., J. Med. Chem., 20, p. 1103–1104 (1977).

Primary Examiner—Donald G. Daus
Assistant Examiner—D. B. Springer
Attorney, Agent, or Firm—William H. Edgerton; Richard D. Foggio; Alan D. Lourie

[57] ABSTRACT

A new group of 2(3H)-indolones whose structures are characterized by having an aminoalkyl substituent at position 4 and a hydroxy group at position 7 of the indolone nucleus have beneficial activity on the cardiovascular system. A typical species of the group is 4-di-n-propylaminoethyl-7-hydroxy-2(3H)-indolone and its acid addition salts.

9 Claims, No Drawings

4-AMINOALKYL-7-HYDROXY-2(3H)-INDOLONES

This invention comprises a new group of 4-aminoalkyl-7-hydroxy-2(3H)-indolones which have a beneficial effect on abnormal conditions of the cardiovascular system.

DESCRIPTION OF THE PRIOR ART

J. Walker et al., J. Med. Chem 13, 983 (1970) report that various benz-hydroxy substituted indolones have little effect on the cardiovascular system. J. D. Loudon et al., Chem. Abs. 50 4963 and G. Wahl, Chem. Abs. 12 2196 also report the preparation of similar compounds. A number of references published by Otsuka Pharmaceutical Company report that certain 8-hydroxy-5-aminohydroxyalkylcarbostyrils have hypotensive and especially broncho-dilating activity; Belgian Patent No. 823,841, J. Med. Chem. 19 1138 (1976) and J. Med. Chem. 20, 1103 (1977). Other Japanese patents issued to Otsuka disclose 5-(α-hydroxy-β-aminoethyl)-oxindoles having vasodilating activity such as Japanese Pat. No. 5,2118-465. Of course serotonin and its position isomers are well known to the art. None of the art known discloses the critical structural features or biological activities of the compounds here claimed.

DESCRIPTION OF THE INVENTION

The compounds of this invention have structures which are characterized by a 2(3H)-indolone (oxindole) nucleus having an aminoalkyl substituent at the 4-position and an oxygen function at the 7-position. They are represented by the following structural formula:

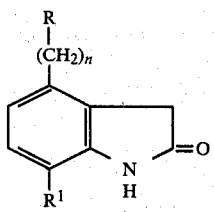

I in which R is amino, lower alkylamino, dilower alkylamino, di-N-allylamino or N-allyl-N-lower alkylamino, $R^1$ is hydroxy or methoxy and n is an integer of from 1-3. Lower alkyl groups will have from 1-6 carbons.

It will be understood that the hydrogen at the 1- or N-position of the indolone nucleus may be tautomeric.

The compounds of Formula 1 which are prime in this invention are those in which $R^1$ is hydroxy. Of these compounds, those having notable biological activity also have n as 2 and R is dilower alkylamino, di-N-allylamino or N-allyl-N-lower alkylamino. A species of this invention is 4-(2-di-n-propylaminoethyl)-7-hydroxy-2(3H)-indolone together with its acid addition salts.

The pharmaceutically acceptable acid addition salts having the utility of the free bases of Formula I are part of this invention. These are prepared by methods well known to the art and are formed with both inorganic or organic acids, for example: maleic, fumaric, benzoic, ascorbic, pamoic, succinic, bismethylenesalicylic, methanesulfonic, ethane disulfonic, acetic, oxalic, propionic, tartaric, salicylic, citric, gluconic, aspartic, stearic, palmitic, itaconic, glycolic, p-aminobenzoic, glutamic, benzenesulfonic, hydrochloric, hydrobromic, sulfuric, cyclohexylsulfamic, phosphoric and nitric acids. The hydrohalic and especially methanesulfonic acid salts are of particular utility.

The compounds of this invention are prepared by the following reaction sequences:

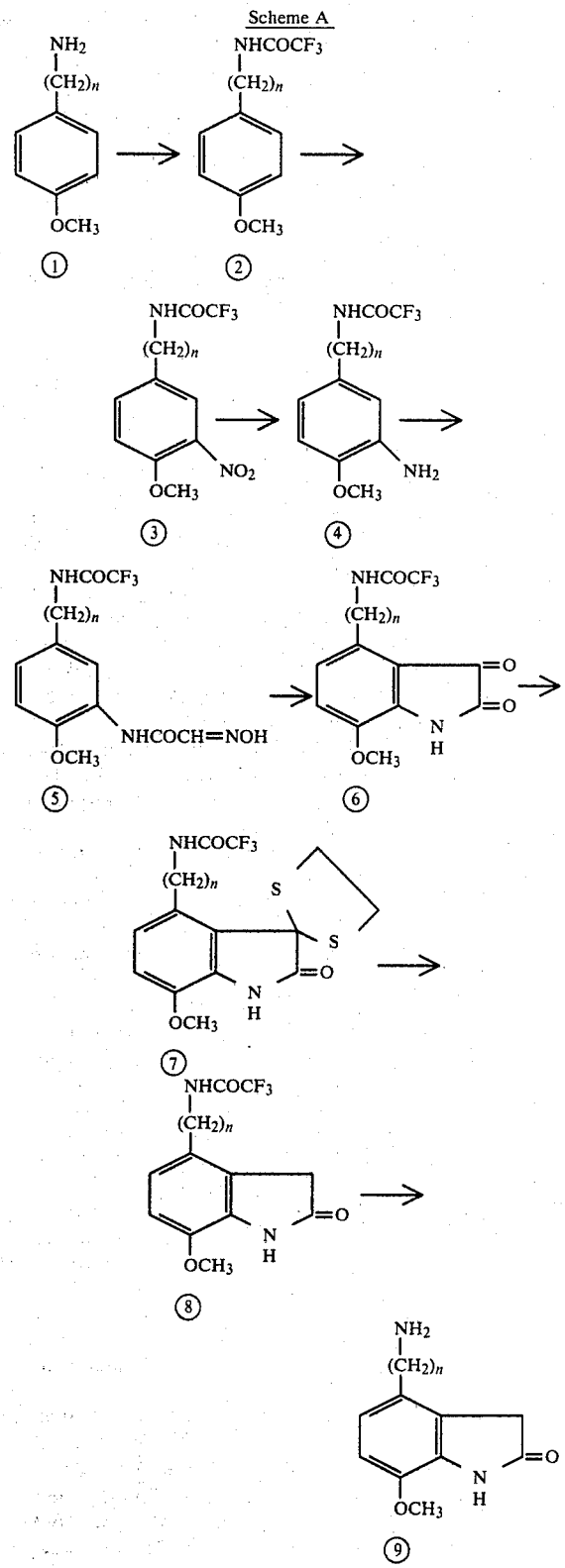

In this scheme n is 1–3.

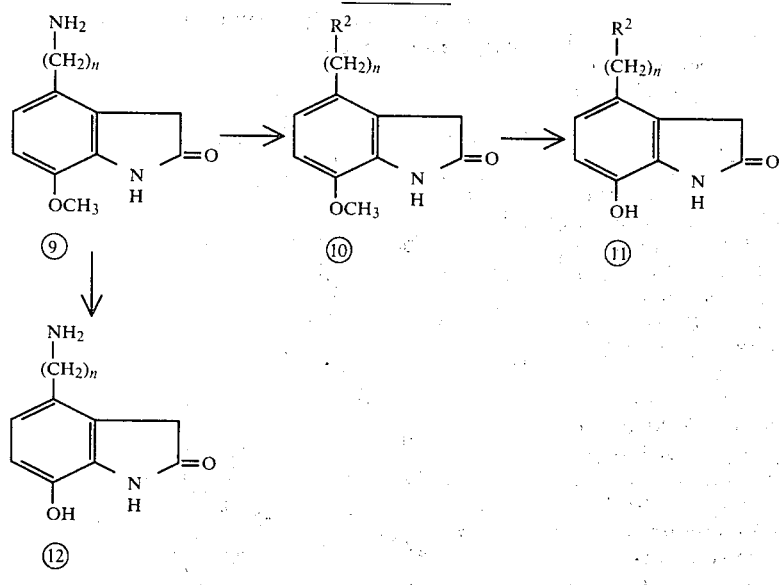

Scheme B

In this scheme $R^2$ is lower alkylamino, diloweralkylamino, N-allyl-N-lower alkylamino or di-N-allylamino and n is 1–3.

The compounds of this invention are prepared by means of a reaction sequence (A above) which features preparing an isatin (6) with an aminoalkyl at position 4 and hydroxy function at position 7 both protected from the reaction conditions of the sequence. The 3-keto group of the isatin nucleus is then removed such as by reaction with ethanedithiol followed by removal of the 3,3-ethylenedithio moiety (7) by hydrogenation. The resulting oxindole (5) is then further reacted to remove the N or O-protective groups after optional N-alkylation which was carried out by standard chemical reactions.

The preparation of the compounds of Formula I in which $R^1$ is hydroxy (i.e. Compounds 11 and 12 of Scheme B above) is accomplished by reacting O-methyl containing compound (i.e. Compounds 9 or 10 of Scheme B) with a dealkylating agent such as hydrobromic acid, hydriodic acid, aluminum chloride, boron tribromide or boron trichloride. The reaction conditions may vary depending on the chemical characteristics of the dealkylating agent. Temperatures from ambient up to reflux temperatures are often used with acid agents such as hydrobromic acid or hydriodic acid which are of course in a water medium.

The use of boron tribromide is most convenient in the cold in a halogenated organic solvent such as methylene dichloride. This procedure is preferred when the desired compound has an N-allyl group present in its structure in order to minimize side reactions at this normally reactive allyl center. If an N-protective group is present and must be removed, the acid reagents are preferred.

The compounds of this invention have a beneficial effect on abnormal cardiovascular conditions especially on the kidney by means of increasing renal blood flow and decreasing renal vascular resistance. Bradycardia is also observed. This activity is domonstrated by monitoring mean arterial blood pressure (MAP), mean renal blood flow (RBF), renal vascular resistance (RVR) and heart rate (HR) by intravenous infusion in the normal anesthetized dog. A clinically effective compound, dopamine, is run in each test for comparison.

As examples of the activity of these compounds in the pharmacological test procedure described, the following results were obtained:

4-(2-di-n-propylamioethyl)-7-hydroxy-2(3H)-indolone hydrobromide (A);

4-(2-di-n-propylaminoethyl)-7-methoxy-2(3H)-indolone hydrochloride (B);

4-(2-aminoethyl)-7-hydroxy-2(3H)-indolone hydrobromide (C);

4-(2-aminoethyl)-7-methoxy-2(3H)-indolone hydrochloride (D).

| Compound | Dose (base) μg/kg/min | % Change MAP | RBF | RVR | HR |
|---|---|---|---|---|---|
| Dopamine | 3 | −13.5* | +22.8* | −29.2* | +2.0 |
| A | 0.3 | −5.1 | +4.6 | −0.5 | +3.6 |
|  | 3 | −24.7* | +24.7* | −39.1* | −11.2* |
|  | 30 | +28.4* | −19.4* | +59.2* | −6.9* |

Administered in 10% dimethylsulfoxide in 0.9% saline.

| Compound | Dose (base) μg/kg/min | % Change MAP | RBF | RVR | HR |
|---|---|---|---|---|---|
| Dopamine | 3 | −6.2* | +23.7* | −23.9* | +1.5 |
| B | 3 | −3.6 | −11.6* | +8.9 | −4.5 |
|  | 30 | −7.8* | +2.8 | −9.5* | −8.3* |
|  | 300 | +0.1 | +0.7 | +1.6 | −7.8* |
| Dopamine | 3 | −5.2* | +33.3* | −28.5* | 0 |
| C | 3 | −10.6* | −12.7* | +4.1 | −2.9 |
|  | 30 | −16.1* | −12.3* | −2.7 | −2.9 |
|  | 300 | +62.6* | −32.7* | +167.0* | −15.8* |
| Dopamine | 3 | −1.4 | +27.7* | −22.4* | +3.3 |
| D | 3 | −0.7 | +6.7* | −7.0 | −1.5 |
|  | 30 | −2.3 | +7.5* | −9.2 | −2.8 |
|  | 300 | −9.8* | +2.1 | −9.4* | −1.6 |

*significant in 2 dogs.

The pharmaceutical compositions of this invention having pharmacodynamic activity in the cardiovascular system, i.e. renal vasodilatation, hypotensive activity and bradycardia, are prepared in conventional dosage unit forms by incorporating a compound of Formula I, or a pharmaceutically acceptable acid addition salt or ester derivative thereof, with a nontoxic pharmaceutical carrier according to accepted procedures in a nontoxic amount sufficient to produce the desired pharmacodynamic activity in a subject, animal or human. Preferably the compositions will contain the active ingredient in an active but nontoxic amount selected from about 25 mg to about 500 mg preferably about 50–250 mg of active ingredient per dosage unit but this quantity depends on the relative potency of the basic compound compared with dopamine as a prototype, the specific biological activity desired, the route of administration whether oral or parenteral, and the condition of the patient.

The pharmaceutical carrier employed may be, for example, either a solid or liquid. Exemplary of solid carriers are lactose, terra alba, sucrose, talc, gelatin, agar, pectin, acacia, magnesium stearate, stearic acid, and the like. Exemplary of liquid carriers are isotonic saline for parenteral use or syrup, peanut oil, olive oil, water and the like for soft gelatin capsules. Similarly the carrier or diluent may include any time delay material well known to the art, such as glyceryl monostearate or glyceryl distearate alone or with a wax. Such sustained release products as well as derivatives which may be gradually metabolized to the active parent can be employed to prolong the unique biological activity of the compounds of this invention.

A wide variety of pharmaceutical forms can be employed. Thus, if a solid carrier for oral administration is used the preparation can be tableted, placed in a hard gelatin capsule in powder, regular or sustained release pellet form, or in the form of a troche or lozenge. The amount of solid carrier will vary widely but preferably will be from about 25 mg to about 1 g. If a liquid carrier is used, the preparation will be in the form of a syrup, emulsion, soft gelatin capsule, sterile injectable liquid such as an ampul, or an aqueous or nonaqueous liquid suspension.

The pharmaceutical preparations are made following the conventional techniques of the pharmaceutical chemist involving mixing, granulating and compressing when necessary, or variously mixing and dissolving the ingredients as appropriate to give the desired end product.

The method of producing improvement in abnormal cardiovacular conditions by inducing renal vasodilatation, antihypertensive effects and bradycardia activity in accordance with this invention comprises administering orally or parenterally to a subject in need of such activity a compound of Formula I or a pharmaceutically acceptable acid addition salt thereof, usually combined with a pharmaceutical carrier, in a nontoxic amount sufficient to produce said activity as described above. The route of administration may be any route which effectively transports the active compound to the cardiovascular system receptors which are to be stimulated such as orally or parenterally, the oral route being preferred. The parenteral administration may be subcutaneous or intravenous. Advantageously, equal oral doses within the ranges given above will be administered several times, such as from one to five times a day, with the daily dosage regimen being selected from about 25 mg to about 1.0 g, preferably 75–500 mg, for oral dosage units. When the method described above is carried out dopaminergic activity is produced. For an average size human for the preferred species (A) a preferred oral dose to show antihypertensive activity would be selected from the range of from about 100–250 mg of base for each dosage unit adapted for oral administration to be administered from 1–5 times daily.

The following examples are designed solely to illustrate the preparation and use of the compounds of this invention. The temperatures are Centigrade. Other variations of these examples will be obvious to those skilled in the art.

EXAMPLE 1

A solution of 50.0 g (0.331 mole) of p-methoxyphenethylamine in 500 ml of dichloromethane was cooled to 0° C. under an argon atmosphere. A solution of 93.6 ml (0.664 mole) of trifluoroacetic anhydride in 60 ml of dichloromethane was added dropwise. The reaction mixture was stirred at 0° for ½ hour then at room temperature for 1½ hours. The volatiles were removed and toluene was added to the residue which was then evaporated. The residue was crystallized from 800 ml of 1:1 ether-petroleum ether to give 55.8 g (68.2%) of a first crop of (2-trifluoroacetamidoethyl)-4-methoxybenzene as white needles, m.p. 84.0° C. Concentration of the mother liquors and recrystallization in 1:1 ether-petroleum ether afforded a second crop of off-white solid, 16.6 g (20.2%), m.p. 82.5°–84.0°.

To a solution of 30 g (0.121 mole) of the amide in 254 ml of trifluoroacetic acid at 0° under an argon atmosphere was added dropwise with stirring a solution of 7.5 ml (0.12 mole) of conc. nitric acid in 56 ml of trifluoroacetic acid. The reaction mixture was stirred at 0° for ½ hour and at room temperature for 2 hours. The solvents were evaporated. The residue was dissolved in ethyl acetate which was extracted with 5% hydrochloric acid, dilute sodium bicarbonate solution and brine, then dried over anhydrous magnesium sulfate and activated charcoal. After filtering, the solvents were removed to give 34.8 g (98%) of crude (2-trifluoroacetamidoethyl)-3-nitro-4-methoxybenzene which was an amber-colored solid. This material was recrystallized from 400 ml of 1:3 ethyl acetate-hexane to give 25.3 g (71.5%) of the product, m.p. 92.5°–93.0°. The mother liquors were concentrated and recrystallized to give a second crop, 4.59 g (13%), m.p. 90°–92° C.

A 50.0 g (0.17 mole) sample of the nitroanisole was hydrogenated in 8–10 g batches using approximately 1.3 g of 10% palladium-on-carbon and 250 ml of absolute ethanol per batch. The hydrogenations were carried out at room temperature and 50–55 p.s.i. hydrogen for ½ to 1 hr. The crude amine was obtained after filtration of the hydrogenation mixtures and evaporation of solvents.

A mixture of 940 ml of distilled water and 11.5 ml (0.207 mole) of conc. sulfuric acid under an argon atmosphere was combined with the total crude amine from above followed by 29.1 g (0.176 mole) of chloral hydrate, 87.5 g (0.533 mole) of hydroxylamine sulfate, and 240 ml distilled water. The mixture was heated rapidly to reflux and was allowed to reflux for 4 minutes then allowed to cool to room temperature. The solid precipitate was separated and washed with 1 liter of cold water and allowed to dry in the air. This solid material was dissolved in hot ethyl acetate and clarified with activated charcoal. Filtration and the addition of hexane at reflux caused recrystallization which gave 27.5 g (50%) of the oxime, m.p. 197°–198°. A second crop was obtained from the mother liquors, 9.9 g (18%), m.p. 192°–195°.

A 50 ml portion of conc. sulfuric acid was heated with stirring under argon in an oil bath maintained at 80° C. To this was added in one portion 5.0 g (0.015 mole) of the oxime. After all the solid mixed into the sulfuric acid the reaction was allowed to continue for 6 minutes at which time the reaction mixture was poured onto 500 ml of ice. The aqueous solution was extracted with several 200 ml portions of ethyl acetate which were combined and washed with sodium bicarbonate solution, brine and then dried over anhydrous magnesium sulfate. The dried solution was filtered through 200 g of silica gel and evaporated to give 3.05 g (64%) of 4-trifluoroacetamidoethyl-7-methoxyisatin as a red solid, m.p. 234°–237°. Recrystallization from ethyl acetate gave material with m.p. 236.5°–238.5°.

A mixture of 23.9 g (0.076 mole) of the isatin, 28.0 ml (0.32 mole) of ethanedithiol and 700 ml anhydrous dichloromethane was stirred at room temperature under argon while 6.3 ml (0.051 mole) of freshly distilled boron trifluoride etherate was added. This reaction mixture was stirred at room temperature overnight (16 hours). After this time an additional 1.0 ml (0.008 mole) of boron trifluoride etherate was added and stirring was continued until thin layer chromatographic analysis indicated that all of the starting material had reacted (about 7 hrs.). The reaction mixture was diluted with 1500 ml of carbon tetrachloride and placed at $-23°$ overnight. The mixture was filtered and washed with cold carbon tetrachloride. The resulting solid was dissolved in an ethyl acetate-ether mixture and extracted with water, bicarbonate, brine and then dried over anhydrous magnesium sulfate-charcoal. Filtration, solvent removal, and recrystallization from ethyl acetate-hexane gave 19.7 g (67%) of first crop product, m.p. 163°–165°. The mother liquors were evaporated and the residue was filtered through 100 g of silica gel (70–230 mesh) to remove origin material. The resulting residue was recrystallized from ethyl acetate-hexane to give an additional 5.6 g (18%) of 3,3-ethylenedithio-4-(2-trifluoroacetamidoethyl)-7-methoxy-2(3H)-indolone.

A 20.0 g (0.051 mole) portion of thioketal was reduced in two batches of 15 g and 5 g amounts. In the 15 g run, approximately 120 g of Raney nickel and 750 ml of absolute ethanol were used. In the 5 g run the amounts were proportional-40 g of Raney nickel and 250 ml of ethanol.

The thioketal was partially dissolved in approximately one-fifth of the total amount of ethanol and was stirred at room temperature under argon. To this was added the Raney nickel along with the remaining ethanol. The reaction mixture was stirred at room temperature until analysis indicated starting material had reacted (2 hrs.). Filtration, copious washing with ethanol, and evaporation gave a crude residue which was taken up in ethyl acetate and extracted with 3 N hydrochloric acid, water, bicarbonate solution, brine and then finally dried over anhydrous magnesium sulfate-active charcoal. Evaporation of the solvents gave a crude residue which was chromatographed on 500 g of silica gel (70–230 mesh). Elution with 10% ethyl acetate-methylene chloride removed most of the colored impurities and 20–50% ethyl acetate-methylene chloride removed the product. Evaporation of the solvents afforded 12.7 g (82%) of 4-(2-trifluoroacetamidoethyl)-7-methoxy-2(3H)-indolone, m.p. 175°–178°. A more careful chromatography gave material with m.p. 178°–179°.

A mixture of 8.0 g (0.026 mole) of the indolone, 59 ml of 6.0 N hydrochloric acid, and 117 ml of absolute ethanol was degassed, filled with argon, and stirred in an oil bath maintained at 90° for ca. 10 hours until analysis indicated no starting material remained. The solvents were removed and the orange solid residue was triturated with ethyl acetate to give 5.56 g (87%) of 4-(2-aminoethyl)-7-methoxy-2(3H)-indolone, hydrochloride as a light-orange solid. This material was recrystallized from methanol-ethyl acetate to give an analytically pure sample of the product, m.p. 258°–260.5°.

Anal. Calcd. for $C_{11}H_{14}N_2O_2 \cdot HCl \cdot \frac{1}{2} H_2O$: C, 52.49; H, 6.41; N, 11.13. Found: C, 52.66; H, 6.44; N, 10.76.

EXAMPLE 2

Sufficient quaternary ammonium polystyrene anion exchange resin ("Amberlite 400", made basic by washing with 1 N sodium hydroxide solution and water) was added to a solution of 0.968 g (4.0 mmole) of the hydrochloride product of Example 1 to give a pH of 9.8. The resin was separated by filtration then washed with water. The aqueous washes were evaporated to give the free base. This base along with 0.425 g of 10% palladium-on-carbon was suspended in 51 ml of glacial acetic acid containing 2.6 ml (0.035 mole) of propionaldehyde and hydrogenated at room temperature and 55 p.s.i. of hydrogen for one hour. The catalyst was separated and washed with acetic acid. Evaporation of the solvents gave a residue which was dissolved in methanol and treated at 0° with a solution of methanolic hydrogen bromide. After several minutes the solvents were removed and the residue was chromatographed on 50 g of silica gel with elution with 4% methanol-chloroform to give 0.439 g of crude tertiary amine. This crude material was dissolved in chloroform to remove residual silica gel. After evaporating the chloroform the resulting residue was recrystallized from methanol-ethyl acetate to afford 0.311 g (21%) of 4-(2-di-n-propylaminoethyl)-7-methoxy-2(3H)-indolone hydrobromide, m.p. 222°–223°.

Anal. Calc'd for $C_{17}H_{26}N_2O_2HBr$: C, 54.33; H, 7.38; N, 7.45. Found: C, 54.28; H, 7.12; 7.48.

In an identical reaction sequence the residue after hydrogenation was treated with ethereal hydrochloric acid. The crude hydrochloride salt (2.2 g) was chromatographed on 40 g silica gel and eluted with 10% methanol-chloroform. After the chloroform trituration, the resulting residue was recrystallized twice from methanol-ether to give 0.346 g (26%) of the hydrochloride salt, m.p. 231°–234°.

Anal. Calc'd for $C_{17}H_{26}N_2O_2 \cdot HCl$: C, 62.47; H, 8.33; N, 8.57. Found: C, 62.51; H, 8.68; N, 8.62.

The hydrochloride salt (100 mg) is mixed with 200 mg of lactose and 2 mg of magnesium stearate, filled into a hard gelatin capsule and administered orally to a hypotensive patient from 2–5 times daily.

EXAMPLE 3

A 0.284 g (0.765 mmole) portion of 4-(2-di-n-propylaminoethyl)-7-methoxy-2(3H)-indolone hydrobromide was placed in a flask and approximately 5 ml of constant boiling hydrobromic acid was distilled (from stannous chloride) directly into the flask. The resulting mixture was stirred at reflux under an argon atmosphere for 3 hours. Evaporation of the solvents produced a solid residue which was recrystallized twice from methanol-ethyl acetate to provide 0.206 g (75%) of 4-(2-din-propylaminoethyl)-7-hydroxy-2(3H)-indolone hydrobromide. m.p. 252°–254°.

Anal. Calc'd for $C_{16}H_{24}N_2O_2$ HBr: C, 53.79; H, 7.05; N, 7.84. Found: C, 53.98; H, 7.00; N, 7.78.

This salt (75 mg) is mixed with 225 mg of lactose and 2 mg of magnesium stearate then filled into a hard gelatin capsule. One capsule is administered orally to patients for treatment of high blood pressure from 1–5 times daily.

The hydrobromide salt (750 mg) is converted to the base as described in Example 2. The base (400 mg) is treated with an excess of methanesulfonic acid in isopropanol and isolated by evaporation and trituration with ether to give the methanesulfonic acid salt. The hydrochloride salt is similarly prepared.

EXAMPLE 4

A 10 ml portion of constant boiling hydrobromic acid (48%) was dissolved from stannous chloride directly into the reaction vessel. To this was added 0.533 g (1.76 mmole) of 4-(2-aminoethyl)-7-methoxy-2(3H)-indolone hydrobromide and the reaction was stirred at reflux under argon for 3 hours then allowed to cool to room temperature. After being stored at 0° overnight, the reaction mixture was filtered. The solid was washed with cold methanol to give 0.40 g (83%) of 4-(2-aminoethyl)-7-hydroxy-2(3H)-indolone hydrobromide as a straw-brown solid. This material began to decompose with darkening at 250°.

Anal. Calc'd for $C_{10}H_{12}N_1O_2$ HBr: C, 43.98, H, 4.80; N, 10.26. Found: C, 43.88; H, 4.86; N, 10.46.

This compound (200 mg) is mixed with 150 mg of lactose and 2 mg of magnesium stearate, filled into a hard gelatin capsule and administered orally 3 times to a patient suffering from cardiovascular disorders caused by renal dysfunction.

EXAMPLE 5

Using 65 g of p-methoxybenzylamine for the starting material of Example 1 gives 4-aminomethyl-7-methoxy-2(3H)-indolone hydrochloride. This material (2 g) was converted to the base and alkylated using 1 mole equivalent of isovaleraldehyde as in Example 2 to give 4-isopentylaminomethyl-7-methoxy-2(3H)-indolone hydrobromide and 4-isopentylaminomethyl-7-hydroxy-2(3H)-indolone hydrobromide after demethylation using boron tribromide in methylene chloride at −20°.

Using 50 g of p-methoxyphenylpropylamine for the starting material of Example 1 gives 4-(3-aminopropyl)-7-methoxy-2(3H)-indolone hydrochloride. This material (3 g) was converted to the base and alkylated using methyl formate-formaldehyde at reflux to give 4-(3-dimethylaminopropyl)-7-methoxy-2(3H)-indolone hydrochloride and, after treatment with boron tribromide in methylene chloride at −20°, 4-(3-dimethylaminopropyl)-7-hydroxy-2(3H)-indolone hydrobromide.

EXAMPLE 6

Using the method of Example 2 but one mole of propionaldehyde in the reductive alkylation procedure gives 4-n-propylaminoethyl-7-methoxy-2(3H)-indolone. Hydrolysis with an excess of 48% hydrobromic acid at reflux gives 4-n-propylaminoethyl-7-hydroxy-2(3H)-indolone hydrobromide.

4-Aminoethyl-7-methoxy-2(3H)-indolone (5 g) is reacted with two mole equivalents of allyl bromide and 4 mole equivalents of triethylamine in acetonitrile at mild heat for several hours. The mixture is then evaporated. The residue is suspended in water. The mixture is extracted with ethyl acetate. The extract is washed, dried and evaporated to give 4-di-N-allylaminoethyl-7-methoxy-2(3H)-indolone. Treatment of an aliquot of the base with methanesulfonic acid in ether-ethanol gives 4di-N-allylaminoethyl-7-methoxy-2(3H)-indolone. Treatment of an aliquot of the base with methanesulfonic acid in ether-ethanol gives 4-di-N-allylaminoethyl-7-methoxy-2(3H)-indolone methanesulfonic acid salt.

Using this compound as the base in the boron tribromide demethylation procedure described above gives 4-di-N-allylaminoethyl-7-hydroxy-2(3H)-indolone hydrobromide.

Using 4-n-propylaminoethyl-7-methoxy-2(3)-indolone (20 g) with one mole equivalent of allyl bromide and two equivalents of triethylamine gives 4-N-allyl-N-propylaminoethyl-7-methoxy-2(3)-indolone base and the hydrochloride salt. The base is treated with boron tribromide to give 4-N-allyl-N-propylaminoethyl-7-hydroxy-2(3)-indolone base and hydrobromide.

What is claimed is:

1. A compound of the structural formula:

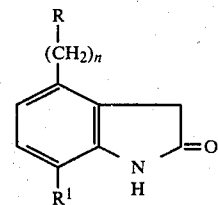

in which R is amino, lower alkylamino, di-loweralkylamino, di-N-allylamino or N-allyl-N-lower alkylamino, $R^1$ is hydroxy or methoxy and n is an integer from 1–3; together with the pharmaceutically acceptable acid addition salts thereof.

2. The compound of claim 1 in which $R^1$ is hydroxy.

3. The compound of claim 1 in which $R^1$ is hydroxy and R is di-n-propylamino, di-N-allylamino or N-allyl-N-propylamino.

4. The compound of claim 1 in which the compound is 4-(2-di-n-propylaminoethyl)-7-hydroxy-2(3H)-indolone.

5. The compound of claim 1 in which the compound is 4-(2-di-n-propylaminoethyl)-7-hydroxy-2(3H)-indolone hydrobromide.

6. The compound of claim 1 in which the compound is 4-(2-di-n-propylaminoethyl)-7-hydroxy-2(3H)-indolone as the base.

7. The compound of claim 1 in which the compound is 4-(2-di-n-propylaminoethyl)-7-methoxy-2(3H)-indolone together with its pharmaceutically acceptable acid addition salts.

8. The compound of claim 1 in which the compound is 4-(2-di-N-allylaminoethyl)-7-hydroxy-2(3H)-indolone together with its pharmaceutically acceptable acid addition salts.

9. The compound of claim 1 in which the compound is 4-(2-aminoethyl)-7-hydroxy-2(3H)-indolone together with its pharmaceutically acceptable acid addition salts.

* * * * *